United States Patent [19]

Inoue et al.

[11] 4,083,969

[45] Apr. 11, 1978

[54] PROCESS FOR PREPARING EASILY ABSORBABLE STEROL GLYCOSIDE

[75] Inventors: Sho Inoue, Uji; Masanobu Kawamata, Oyamazaki; Hirokazu Ushimaru, Kyoto; Koichi Nakamichi, Kyoto; Yutaka Takahashi, Kyoto, all of Japan

[73] Assignee: Nippon Shinyaku Co., Ltd., Kyoto, Japan

[21] Appl. No.: 674,432

[22] Filed: Apr. 7, 1976

[30] Foreign Application Priority Data

Apr. 8, 1975 Japan .................................. 50-43008

[51] Int. Cl.$^2$ ..................... C07J 17/00; A61K 31/705
[52] U.S. Cl. ........................................ 424/182; 536/5; 536/6; 536/7
[58] Field of Search ...................... 424/182; 536/18, 5

[56] References Cited

U.S. PATENT DOCUMENTS

| 3,862,931 | 1/1975 | Kaiser et al. .............................. 536/5 |
| 3,966,918 | 6/1976 | Kawamata et al. ...................... 536/5 |

FOREIGN PATENT DOCUMENTS 1,298,047  11/1972  United Kingdom ..................... 536/5

*Primary Examiner*—Johnnie R. Brown
*Attorney, Agent, or Firm*—Jacobs & Jacobs

[57] ABSTRACT

Sterol glycosides are rendered easily absorbable through the digestive tract by dissolving or dispersing the steroid glycoside with heating into a water solution of a polymer or polymers and then removing the solvent.

4 Claims, 2 Drawing Figures

Key:
- ⊙——⊙ Soluble starch;
- □——□ Polyvinylacetaldimethylaminoacetate
- ●——● Dimethylaminoethylmethacrylate-methylmethacrylate copolymer
- ◐——◐ Polyvinylalcohol;
- △——△ Dextrin
- ×——× Starch alphalized by enzyme;
- ▲——▲ Polyvinylpyrrolidone
- ○——○ Hydroxypropylstarch

PROCESS FOR PREPARING EASILY ABSORBABLE STEROL GLYCOSIDE

DETAILED DESCRIPTION

Figure 1:
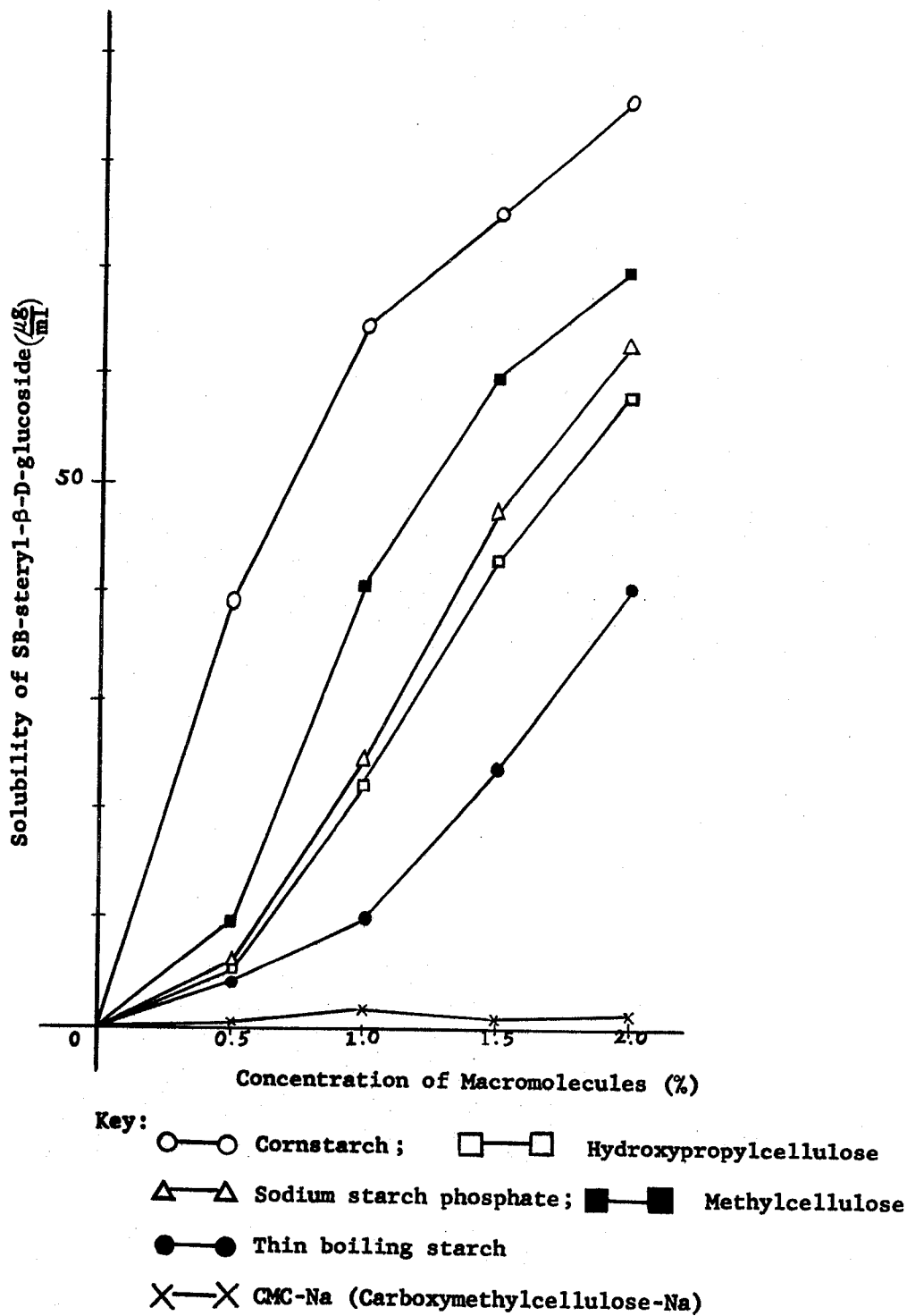

This invention relates to a process for preparing sterol glycosides in a form which is easily absorbed in the digestive tract. Sterol glycosides occur widely in plants in its own form or in a form of fatty acid ester and can be extracted from natural sources, such as soybeans, cotton seeds, kapok seeds, chick pea seeds, Oenophera erythrosepara root, etc.; see e.g. Kiribuchi et al., Agr. Biol. Chem. 30, No. 8, 770–778 (1966). In this form it is principally a mixture of beta-sitosterol-beta-D-glucoside, stigmasterol-beta-D-glucoside, campesterol-beta-D-glucoside, and the like. Beta-sitosterol-beta-D-glucoside, stigmasterol-beta-D-glucoside, campesterol-beta-D-glucoside, cholesterol-beta-D-glucoside, and the like can also be synthesized by known processes; see e.g., Chem. Ber. 105, 1097–1121. Sterol glycosides from either source are important in medicine as a result of their strong hemostatic property.

As will be seen below, no significant difference of pharmacological activity on oral administration is observed by reason of the particular sterol in these glucosides. The activity of sterol glucosides extracted from soybeans (hereinafter abbreviated as "SB sterol-$\beta$-D-glucoside", which is a mixture of about 55% $\beta$-sitosterol-$\beta$-D-glucoside, about 20% stigmasterol-$\beta$-D-glucoside and about 25% campesterol-$\beta$-D-glucoside, is not significantly different from that of the individual components.

Sterol glycosides are comparatively well soluble in solvents such as pyridine, dioxane and dimethylformamide but insoluble in other solvents such as water, methanol, acetone, chloroform, benzene, hexane and ether. Most significant for pharmaceutical purposes is the fact that the compounds are nearly insoluble in water and cannot be applied in its own form as medicine because of poor absorptivity in the digestive tract. For example when administered as a water solution using a solubilizer, the minimum effective dose is 2 mg/kg (P < 0.05). When administered simply in suspension, the minimum effective dose is 32 mg/kg. Being almost insoluble in water, the solid material is not well absorbed.

Absorption of these compounds through digestive tracts is not increased by known means such as pulverization into fine particles. Several proposals for the preparations of peroral administrative forms however have been proposed (see Dutch Patent Application No. 01301/1973, German Pat. No. 2,303,247, and British patent specification No. 1,298,047). Thus the glycosides are dissolved in ethanol, which solution is then combined with fine particles of talc, starch or aerosil. The solvent is then removed and the steryl-glucoside is adsorbed on the surface of the particles. Alternatively, a steryl-glucoside is dissolved in ethanol and this solution is mixed with a vegetable oil emulsion containing a natural emulsifying agent. These compositions have been prepared and their hemostatic activities observed. As will be seen below (Table 2, Nos. 7, 8 and 9), either the minimum effective doses were no better than the minimum effective doses of suspensions of the original powders or pharmacological effects were not observed at these doses. It would not appear that these compositions enhance the availability of steryl-glucosides.

The present invention relates to a process of preparing sterol glycosides in a form which is easily absorbed through the digestive tract. Briefly the sterol glycoside is dissolved or dispersed with heating in a water solution of a water soluble or dispersible polymer or polymers. These include water soluble vinyl or acrylic polymers, starch, modified starch including water soluble starch derivatives, cellulose derivatives and gum arabic. Typical vinyl polymers include polyvinylpyrrolidone, polyvinyl alcohol and polyvinyl acetal diethylaminoacetate (AEA, Sankyo K. K.). A typical acrylic polymer is diethylaminoethyl methacrylate/methyl methacrylate copolymer (EUDRAGIT E, Rohm & Haas). Starch or modified starch include natural starch obtained from corn, potato or arrowroot, alphalized starch, (AMYCOL, Nichi-Den Kagaku), dextrin, thin boiling starch, (LUSTERGEN, NSP, Nichi-Den Kagaku), and soluble starch. Water soluble starch or cellulose derivatives such as esterified starch (sodium starch phosphate), hydroxypropyl cellulose, methyl cellulose, and the like can also be used.

To aqueous solutions of the above polymers, are added the sterol glycoside. While heating at 40° C or above, preferably 50° – 80° C, the solution is dispersed by means of a homogenizer or a homogenizing mixer. During the dispersion, a small amount of surface active agent can be added to improve the wetting effect on sterol glycoside, and make the dispersion easier. Two or more polymers can of course be used in mixture to vary the dispersibility and viscosity. The ratio of sterol glycoside to polymer is generally within a range from about 1:2 to about 1:10.

The solvent is next removed as by heating with a rotary evaporator under reduced pressure, freeze-drying process, spray-drying, or the like.

Figure 2:
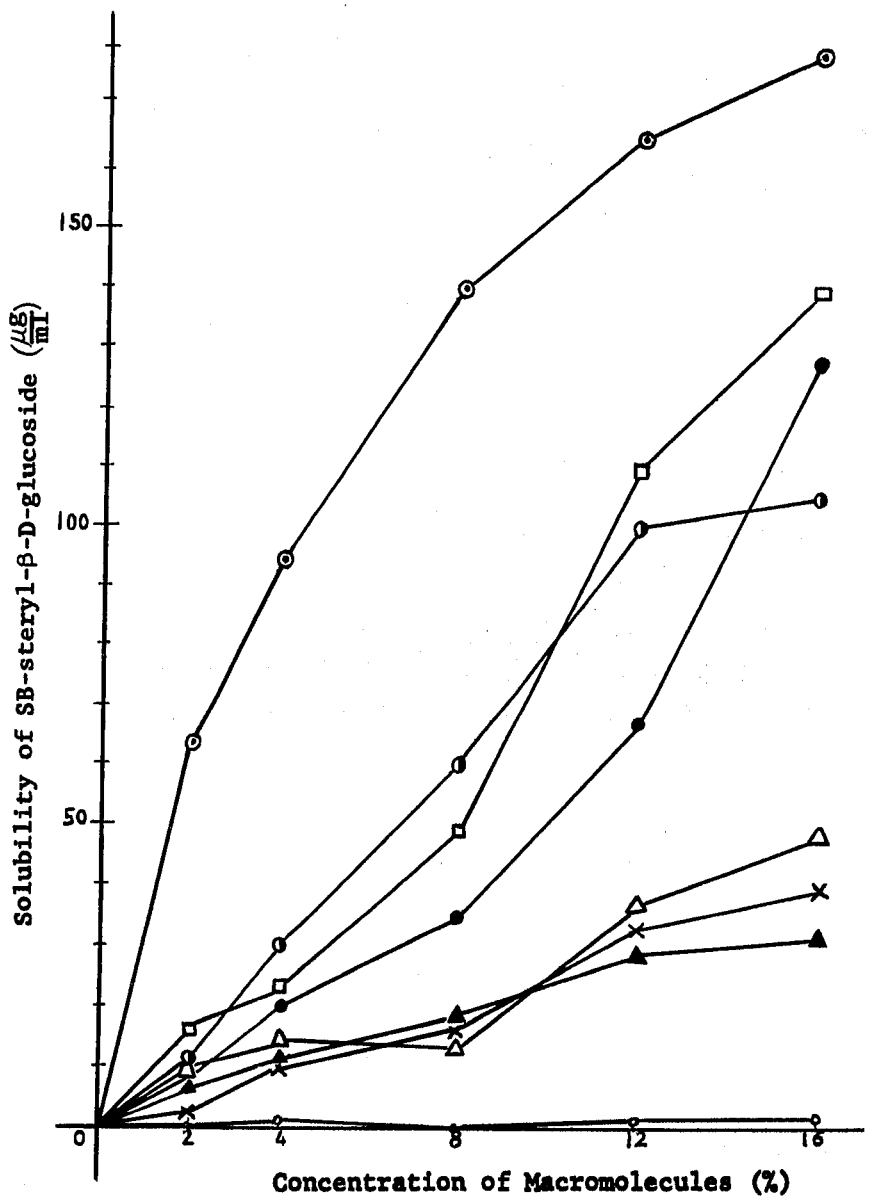

The polymer and sterol glycoside interact in water solution. FIGS. 1 and 2 show the solubility of SB sterol-$\beta$-D-glucoside after shaking for 24 hours at 25° C at various concentrations of polymer. An excess amount of SB sterol-$\beta$-D-glucoside is added to water solution of polymer at various concentrations, shaked for 24 hours at 25° C and filtered with a membrane filter. Then SB sterol-$\beta$-D-glucoside in the filtrate is measured by Liebermann-Burchard reaction after separation of polymers through the silica gel column.

Polymers which do not influence solubility, such as sodium carboxymethylcellulose or etherified starch (PIOSTARCH, Nichi-Den Kagaku) produced only the same effect as that of the raw powder. Thus the apparent increase in solubility with the polymers of the present invention accelerates absorption through the digestive tract.

The hemostatic activity upon amputation of the tail tip in mice after administration of 32 mg/kg of SB sterol-$\beta$-D-glucoside [see J. Jikei Univ. Sch. of Med., 75 (5) 1008 (1959)] is as follows:

Table I

| Hours after Administration | Hemostatis (mins) | Sign. Diff |
|---|---|---|
| Control | 14.26 ± 1.47 | — |
| 1 | 12.6 ± 1.37 | — |
| 2 | 10.7 ± 1.21 | (P<0.05) |
| 3 | 11.61 ± 1.45 | — |
| 4 | 12.65 ± 1.61 | — |

Table II demonstrates the heomostatic properties of various materials and compositions, measured 2 hours after administration.

TABLE II

| No. | Steryl-glucoside | Polymer/Carrier | Procedure | Hemostatic Activity in Mice (Minutes) | | | | | | Control |
|---|---|---|---|---|---|---|---|---|---|---|
| | | | | 64 mg/kg | 32 mg/kg | 16 mg/kg | 8 mg/kg | 4 mg/kg | 2 mg/kg | |
| 1 | A | — | — | 8.1±1.1** | 9.1±1.3* | 11.1±1.4 | — | — | — | 13.5±1.0 |
| 2 | B | — | — | 9.0±0.8** | 9.8±0.9* | 12.3±1.1 | — | — | — | 13.5±1.0 |
| 3 | C | — | — | 8.9±1.0** | 9.4±1.2* | 11.9±1.3 | — | — | — | 13.5±1.0 |
| 4 | D | — | — | 8.7±1.0** | 9.7±1.1* | 12.0±0.9 | — | — | — | 13.5±1.0 |
| 5 | E | — | — | 8.9±0.9** | 9.6±1.1* | 12.6±1.2 | — | — | — | 13.5±1.0 |
| 6 | E | Solution | (a) | — | — | — | — | 7.9±0.7 | 9.3±0.9 | 13.5±1.0 |
| 7 | A | Talc (X10) | Dutch Appln. 7,301,301 Ex. 1 | — | 13.1±1.7 | 14.8±1.0 | 12.2±1.5 | — | — | 13.9±1.7 |
| 8 | A | Cornstarch (X10) | British No. 1,298,047 Ex. 2 | — | 10.1±1.4* | 12.2±2.0 | 11.4±1.5 | — | — | 13.9±1.7 |
| 9 | A | Emulsion | British No. 1,298,047 Ex. 1 | 12.4±1.1 | 13.2±1.6 | 11.0±1.4 | 11.9±1.1 | — | 13.6±1.0 | |
| 10 | D | Cornstarch | Ex. 1 (X10) | — | — | 9.6±0.8** | 10.7±1.1* | 12.9±1.1 | — | 14.7±1.3 |
| 11 | E | Polyvinylpyrrolidone (MW≈10⁴) | Ex. 2 (X10) | — | — | 10.3±1.2* | 10.6±1.0* | 12.3±1.4 | — | 13.4±0.6 |
| 12 | E | Enzymatic alphalized starch | Ex. 3 (X10) | — | — | 9.5±0.8** | 10.2±1.2* | 11.3±1.1 | — | 14.7±1.2 |
| 13 | B | Polyvinylacetal diethylaminoacetate | Ex. 1 (X5) | — | — | 9.0±1.0** | 9.9±1.1* | 10.5±0.8* | 11.7±1.3 | 14.7±1.2 |
| 14 | E | Diethylaminomethylmethacrylate/methyl methacrylate copolymer | Ex. 1 (X5) | — | — | 9.2±1.2** | 10.3±1.2 | 12.0±1.1 | — | 14.7±1.2 |
| 15 | A | Polyvinylpyrrolidone | Ex. 1 (X10) | — | — | — | 9.4±1.1** | 10.6±1.1* | 11.5±1.2 | 14.7±1.2 |
| 16 | C | Hydroxypropylcellulose | Ex. 1 (X10) | — | — | — | 8.6±0.9** | 9.3±0.7* | 9.9±1.0 | 12.6±0.9 |
| 17 | E | Dextrin | Ex. 1 (X10) | — | — | — | 9.0±0.8 | 10.5±0.9 | 11.5±1.2 | 12.4±1.0 |
| 18 | E | Thin boiling starch | Ex. 1 (X10) | — | — | — | 9.1±1.0** | 10.0±0.8 | 11.4±1.2 | 12.4±1.0 |
| 19 | A | Sodium starch phosphate | Ex. 1 (X10) | — | — | — | 8.9±0.9 | 10.0±0.7 | 11.5±1.3 | 12.4±1.0 |
| 20 | E | Soluble starch | Ex. 1 (X10) | — | — | 8.5±0.6** | 9.6±1.0* | 10.3±0.9 | — | 12.4±1.0 |
| 21 | E | Alphalized starch | Ex. 1 (x10) | — | — | 9.6±0.6** | 10.4±1.0* | 12.8±1.1 | — | 14.7±1.2 |
| 22 | E | Methylcellulose | Ex. 1 (X10) | — | — | 9.7±0.7** | 10.9±1.1* | 12.0±1.2 | — | 14.7±1.2 |
| 23 | E | Polyvinyl alcohol | Ex. 1 (X10) | — | — | — | 9.3±0.8** | 10.1±0.7 | 11.6±0.7 | 12.4±1.0 |
| 24 | E | Sodium carboxymethylcellulose | Ex. 1 (X10) | — | 10.9±0.8 | 11.1±1.0 | 12.9±1.4 | — | — | 13.8±1.2 |
| 25 | E | Hydroxypropyl starch | Ex. 1 (X10) | — | 10.6±1.2 | 13.6±1.0 | 13.3±1.2 | — | — | 13.8±1.2 |

Notes
A = β-sitosteryl-β-D-glucoside
B = Stigmasteryl-β-D-glucoside
C = Campesteryl-β-D-glucoside
D = Cholesteryl-β-D-glucoside
E = Soybean steryl-β-D-glucoside
*($P<0.05$)
**($P<0.01$)
(a)20 mg of glucoside dissolved in 20 ml ethanol and polyoxyethylene (60 mol) ether of hydrogenated castor oil; hot water added q.s. 100 ml.

As can be seen from Table II, no significant difference results from variations in the aglycones (compare Nos. 1-5). Prior art methods (Nos. 7-9) do not enhance activity over that observed with a solution using a solubilizer (No. 6). For soluble polymer composition according to the invention (Nos. 10-23), the minimum effective dose in from about 4 to about 8 mg/kg (P 0.05).

The material is administered orally in any of the usual solid pharmaceutical forms such as tablets, capsules or powders, including sustained release preparations. The term unit dosage form as used in this specification and the claims refer to physically discrete units to be administered in single or multiple dosage to animals, each unit containing a predetermined quantity of active material in association with a carrier. The quantity of active material is that calculated to produce the desired therapeutic effect upon administration of one or more of such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added improve the availability of the medicament when the capsule is ingested.

Tablets are made by preparing a powder mixture, granulating or slugging, adding a lubricant and disintegrant and pressing into tablets. A powder mixture is prepared by mixing the compound, suitable comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A protective coating consisting of a sealing coat of shellac, a coating of sugar or polymeric material and a polish coating of wax can be provided. Dyestuffs can be added to these coatings to distinguish different unit dosages.

The following examples will serve to further typify the invention.

EXAMPLE 1

In about 200 ml of water, 3.6 g of corn starch were dissolved with heat, and 0.4 g of cholesterol-$\beta$-D-glucoside was added. The mixture was dispersed at 60° C for 1 hour using a homogenizing mixer, and then water was removed by a rotary evaporator. About 4 g of the component was obtained.

EXAMPLE 2

In about 50 ml of water, 4.5 g of polyvinylpyrrolidone (PVPK-15, molecular weight $10^4$) were dissolved, and 0.5 g of SB-sterol-glucoside was added. The mixture was dispersed at about 50° C for 15 minutes using an ultrasonic homogenizer, and then freeze-dried. About 5 g of the component were obtained.

EXAMPLE 3

In 10 liters of 0.1% solution of HCO60, 2.7 kg of starch alphalized by enzyme (AMYCOL No. 1, Nichi-Den Kagaku) were dissolved and 300 g and of SB sterol glucoside were added. The mixture was dispersed for about 20 minutes using a whistling ultrasonic homogenizer (made by Ultra Sonic Co.) and spray-dried using an atomizing spray-dryer. About 3 kg of the fine powder were obtained.

Polyvinyl acetal diethylaminoacetate, dimethylaminoethyl methacrylate/methyl methacrylate copolymer, polyvinylpyrrolidone, hydroxypropyl cellulose, dextrin, thin boiling starch, sodium starch phosphate soluble starch, alphalized starch, methyl cellulose, polyvinylpyrrolidone, and polyvinyl alcohol, were processed in accordance with Example 1 to yield similar products.

What is claimed is:

1. A composition comprising a mixture of (a) one or more steryl glucosides selected from the group consisting of $\beta$-sitosteryl-$\beta$-D-glucoside, stigmasteryl-$\beta$-D-glucoside, campesteryl-$\beta$-D-glucoside, and cholesteryl-$\beta$-D-glucoside and (b) at least one water soluble polymer selected from the group consisting of polyvinylpyrrolidone, polyvinyl alcohol, polyvinyl acetal diethylaminoacetate, diethylaminoethyl methacrylate/methyl methacrylate copolymer, starch, modified starch, alphalized starch, dextrin, sodium starch phosphate, hydroxypropylcellulose and methyl cellulose, said mixture being the solid residue remaining after removal of water from an aqueous solution of said glucoside and said polymer.

2. A composition according to claim 1 wherein the steryl glucoside is a mixture of $\beta$-sitosteryl-$\beta$-D-glucoside, stigmasteryl-$\beta$-D-glucoside and campesteryl-$\beta$-D-glucoside.

3. An oral hemostatic pharmaceutical composition comprising an effective amount of a composition according to claim 1 and a pharmaceutically acceptable carrier.

4. The method of effecting a hemostatic response in humans and other animals which comprises orally administering an effective amount of a composition according to claim 1.

* * * * *